United States Patent [19]

Kim et al.

[11] Patent Number: 4,987,183

[45] Date of Patent: Jan. 22, 1991

[54] CATIONIC RESIN HAVING U.V. ABSORBERS AND THE PROCESS FOR PRODUCING THE ABSORBERS

[75] Inventors: Young D. Kim; Byung J. Ha, both of Seoul, Rep. of Korea

[73] Assignee: Pacific Chemical Co., Ltd., Seoul, Rep. of Korea

[21] Appl. No.: 368,704

[22] Filed: Jun. 20, 1989

[30] Foreign Application Priority Data

Jun. 20, 1988 [KR] Rep. of Korea ............... 1988-7413

[51] Int. Cl.$^5$ .............................................. C08F 8/30
[52] U.S. Cl. ................................... 525/59; 525/281
[58] Field of Search ............................ 525/59, 281

[56] References Cited

U.S. PATENT DOCUMENTS

| | | | |
|---|---|---|---|
| 2,476,832 | 7/1949 | Donia | 525/281 |
| 4,254,244 | 3/1981 | Gates et al. | 525/59 |
| 4,778,847 | 10/1988 | Schornick et al. | 525/59 |
| 4,891,300 | 1/1990 | Ichimura et al. | 525/59 |

FOREIGN PATENT DOCUMENTS 60-258148  5/1987  Japan.
1230453  5/1971  United Kingdom.

*Primary Examiner*—Bernard Lipman
*Attorney, Agent, or Firm*—Millen, White & Zelano

[57] ABSTRACT

The present invention relates to a novel cationic polymer processing U.V. absorbing ability which is produced by the ester bonding of a cationic U.V. absorber to the terminal of the polymer. Unlike conventional nonionic U.V. absorbing polymers or nonionic or anionic U.V. absorbers, the U.V. absorber according to the present invention exhibits an improved substantivity to several anionic substrates, for example, hair, skin, and the like, due to the presence of a positively charged substituent group.

5 Claims, 2 Drawing Sheets

U.V. ABSORPTION SPECTRUM

I.R. ABSORPTION SPECTRUM

CATIONIC RESIN HAVING U.V. ABSORBERS AND THE PROCESS FOR PRODUCING THE ABSORBERS

FIELD OF THE INVENTION

The present invention relates to a resin having the U.V. absorbing group of the following general formula (I) and the process for producing the same.

The object of this invention is to provide the process for producing the compound of the general formula (I):

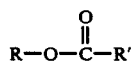

wherein R—O is the moiety representing polymer, which includes vinyl pyrrolidone/vinyl acetate/vinyl alcohol polymer, vinyl pyrrolidone/vinyl alcohol polymer, vinyl formal/vinyl alcohol/vinyl acetate polymer, vinyl butyral/vinyl alcohol/vinyl acetate polymer, guahydroxy propyltrimethyl ammonium chloride, alpha-[2-hydroxy-3-(trimethyl ammonio)propyl]-w-hydroxy poly (oxy-1,2-ethandiyl)chloride cellulose-ω-ether;

R' represents

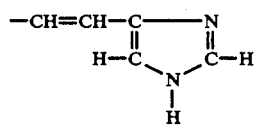

or

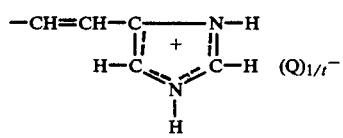

wherein t is an integer which is equal to the valence of Q and Q is an anion such as chloride, bromide, iodide, sulfate, nitrate, sulfonate, phosphate, acetate, and the like.

The compound (I) of the present invention can be prepared by esterification of the above-defined R by way of nucleophilic substitution of it with urocanic acid, urocanic ethyl ester, urocanic acid of which the nitrogen atom of imidazole is protected with tosyl group or t-butoxycarbonyl, or their derivatives.

DESCRIPTION OF THE RELATED ART

Urocanic acids usually present in epithelial layer of the skin and also contained in sweat, have been widely used as a low-irritating natural U.V. absorber in cosmetics [see: Cosmetics & Toiletries, Vol 98, 47–50 (1983)]. They have been developed in the type of ethylester, and the like due to their high water-solubilizing property; however, when they are used as an additive in external cosmetics such as skin care products or hair care products they exhibit poor maintenance since they can be readily removed by sweat or sebum components secreted from the skin.

Recently, a variety of cationic resins have been developed and used in cosmetics, especially hair care products such as shampoo or rinse, and they have been found to have excellent maintenance and adhesion - ability [see. U.S. Pat. No. 3,472,840]. It has also been proved from the relevant literature that, when the cationic resin is added to hair care products, they show good substantivity to the hair surface having anionic character, retain maintenance for a long period of time and prevent the generation of static electricity [see. Textile Research Journal, No. 9, 616–620 (1977)].

Accordingly, the present inventors found that when the resin used for cosmetics is cationized by bonding it with an U.V. absorber showing poor maintenance, the resulting product exhibits excellent maintenance and adsorption ability to the hair or skin surface, and at the same time prevents the generation of static electricity in hair. In contrast, the conventional high-molecular U.V. absorber could not make interaction of static electricity with the hair or the skin since they have an almost non-ionic character (see. Y. H. Oda, Polymer Finechemical, Koudan Press, 1982, pp. 150–152).

SUMMARY OF THE INVENTION

The object of the present invention is to solve the above-mentioned problems presented by the conventional U.V. absorbers and to provide the process for producing a cationic resin having U.V. absorber which is characterized in exhibiting an excellent maintenance to the hair or the skin and particularly preventing the generation of static electricity in hair.

It has been generally known that the introduction of a cationic group into an U.V. absorber improves the maintenance of the U.V. absorber to the hair or skin; however, there is almost no concrete illustration [see. Cosmetics & Toiletries, Vol. 102, p 71–80 (1987)]. The known literature only describes that an U.V. absorber is bonded with an N-alkyl group having a long chain and then cationized to give an U.V. absorber substituted with quaternery ammonium.

Therefore, the present inventors, perceiving the previously mentioned facts, introduced an U.V. absorber into the polymer and then cationized it to produce an U.V. absorber having improved affinity to the hair or skin and as a result they have completed this invention.

DETAILED DESCRIPTION OF THE INVENTION

More specifically, the object of the present invention can be achieved by the process which comprises reacting the compound of the general formula (II) with the compound of the general formula (III) to give a cationic resin having an U.V. absorbing group of the general formula (I):

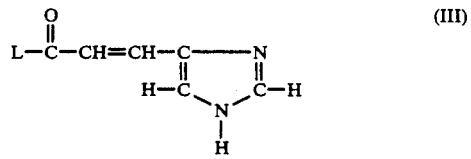

wherein R—O is as defined above, and the specific structures thereof are as follows:

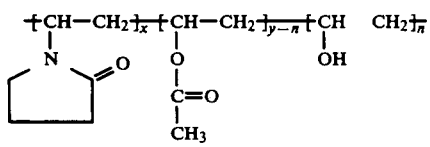

vinyl pyrrolidone/vinyl acetate/vinyl alcohol polymer

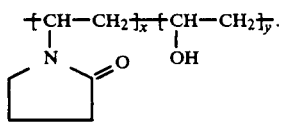

vinyl pyrrolidone/vinyl alcohol polymer

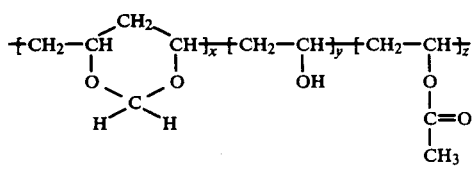

vinyl formal/vinyl alcohol/vinyl acetate polymer

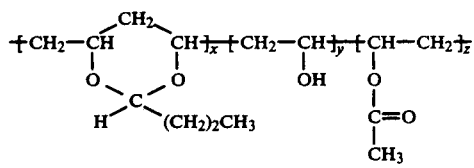

vinyl butyral/vinyl alcohol/vinyl acetate polymer

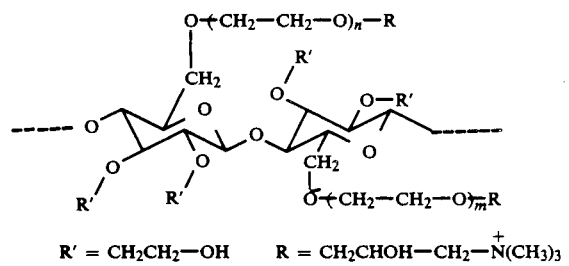

R' = CH₂CH₂—OH    R = CH₂CHOH—CH₂—N⁺(CH₃)₃ alpha-(2-hydroxy-3-(trimethylammonio)propyl)-ω-hydroxy poly (oxy-1,2-ethandiyl)chloride cellulose-ω-ether

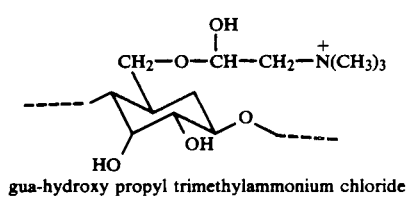

gua-hydroxy propyl trimethylammonium chloride

In compound (III) L represents a leaving group, particularly chloride, bromide, iodide, hydroxy, ethoxy or methoxy group.

Compound (I) is the novel one which is first revealed by the present invention and has never been described in any other conventional method.

The compound (I) according to the present invention can be prepared by the process described hereinafter.

(A) The compound of the general formula (I) can be prepared by the reaction of compound (II) with compound (III) according to the following reaction scheme:

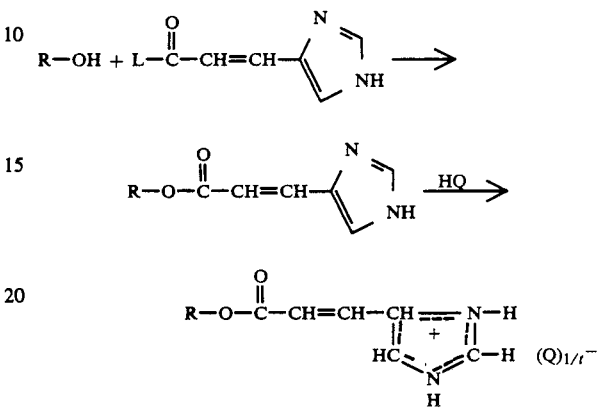

wherein R—O and L are as defined above. More specifically, the reaction is carried out by swelling the compound (II) sufficiently in polar aprotic solvent or aprotic solvent and then reacting with compound (III). When L in compound (III) is —OH, a coupling reagent may be used to accelerate the reaction. The coupling reagents may include, for example, N,N'-dicyclohexyl carbodiimide, 1,1-carbonyldiimidazole, N-ethyloxycarbonyl-2-ethyloxy-1,2-dihydroquinolin, N-isobutyloxycarbonyl-2-iso-butyloxy-1,2-dihydro-quinolin. Among these, 1,1-carbonyldiimidazole is most effective. Suitable reaction solvents used in this reaction may include, for example, dichloromethane, dimethylformamide, tetrahydrofuran, dioxane, and the like, which can be used as a single or, if necessary, as a mixture of in appropriate ratio. The reaction temperature and period varies depending on the type and structure of starting material (II). In general, the reaction temperatures are within a range of −5° C. to 120° C., preferably 0° C. to 100° C., and the reaction periods are from 10 minutes to 72 hours, preferably 1 hour to 48 hours. The compound of formula (I) is formed by adjusting the pH of the above solution in the range of 5 to 6 with a suitable acid. Then, if necessary, gel chromatography may be carried out to remove impurities.

(B) Among the compounds of the general formula (II), vinyl pyrrolidone/vinyl alcohol polymer, vinyl pyrrolidone/vinyl acetate/vinyl alcohol polymer can be prepared by the hydrolysis of polyvinyl pyrrolidone/vinyl acetate copolymer according to the following reaction scheme:

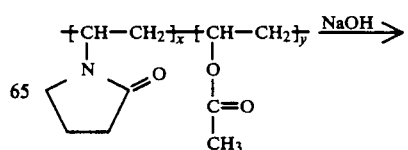

-continued

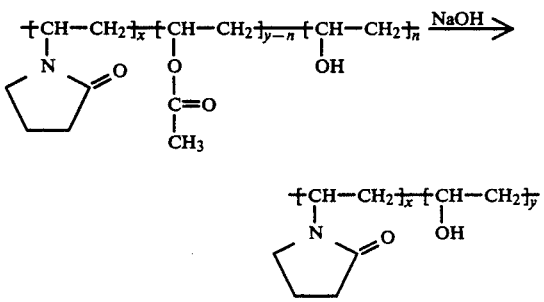

wherein x represents a degree of polymerization of vinyl pyrrolidone; y represents a degree of polymerization of vinylacetate or vinyl alcohol; and y-n and n represent a degree of polymerization of vinylacetate and vinyl alcohol, respectively, which already hydrolyzed partially. The hydrolysis may be carried out completely to produce a vinyl pyrrolidone/vinylalcohol polymer or partially to produce a vinyl pyrrolidone/vinyl acetate/vinyl alcohol polymer depending on the reaction period and/or the reaction temperature. The ratio of vinyl acetate to vinyl alcohol can be controlled by the reaction period and/or the reaction temperature.

(C) The polyvinyl pyrrolidone/vinylacetate copolymer used in the above (B) can be prepared by free radical polymerization [see: Bayer, E and Geckeler, K, Justus Liebigs Ann. Chem., 10, 1671–4 (1974)]. The reaction scheme is as follows:

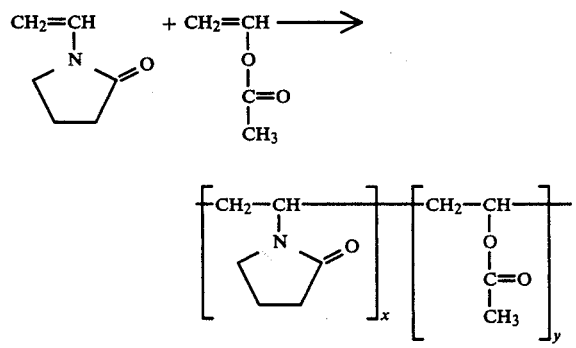

More specifically, the reaction is carried out by refluxing and stirring 1.5 equivalent of 1-vinyl-2-pyrrolidone, 1 equivalent of vinyl acetate and catalytic amounts of 2,2'-azodiisobutyronitrile for 1 hour under a nitrogen atmosphere. After reducing the reaction temperature, the stirring is continued for 15 hours at 30° C. and then the reaction is finished. The excess amount of cyclohexane is added, and the resulting precipitates are obtained by filtering and drying. In the above formula, X and Y are as defined above.

The compound (I) according to the present invention can be used as a constituent of cosmetics, for example, hair care products such as shampoo, hair rinse, hair mousse, hair gel, hair spray, and the like and skin care products such as day cream, sunscreen cream and lotion and make-up cosmetics such as foundation, compact, and the like. Particularly when used as an additive in hair care products, compound (I) protects the hair from damage of lackluster, discoloration or fading due to the sun, particularly U.V. light. And also, when used as an additive in the basic or make-up cosmetics, they retard effectively the aging of skin and excessive sunburning.

The conventional U.V. absorbers are usually lipophilic oil or hydrophilic anionic salt; the former has an excessively oily property and is poor in use with an aqueous base and the latter is readily cleansed by water due to its poor adhesion-ability to the hair or skin, which accompanies the problem of maintenance.

While the U.V. absorber according to the present invention has cationic character and is a film-forming polymer, they can improve the substantivity to the hair having anionic character, prevent the generation of static electricity, have an excellent hair conditioning effect and is not readily removed by water, so it is useful in hair care products for summer.

In addition, when used in basic and make-up cosmetics as previously mentioned, the U.V. absorber of this invention can be spread and applied uniformly on the skin with excellent substantivity and water-resistance. This provides high maintenance of effect with the summer sunscreen basic and make-up cosmetics using it.

The compounds (I) and compounds (II) according to the present invention may be used singly, but they are usually mixed with a carrier to make use as a cosmetic easier.

The preparations according to the present invention do not need particular conditions. They can be formulated as emulsions, aerosols and solubilizing products by known techniques in the art and used in a variety of ways.

The preparations for preventing U.V. light produced by the process of the present invention contain as an effective ingredient in the range of 0.001 to 40% by weight, preferably 0.02 to 5% by weight of the compound (I)

EXAMPLES

Figure 1:
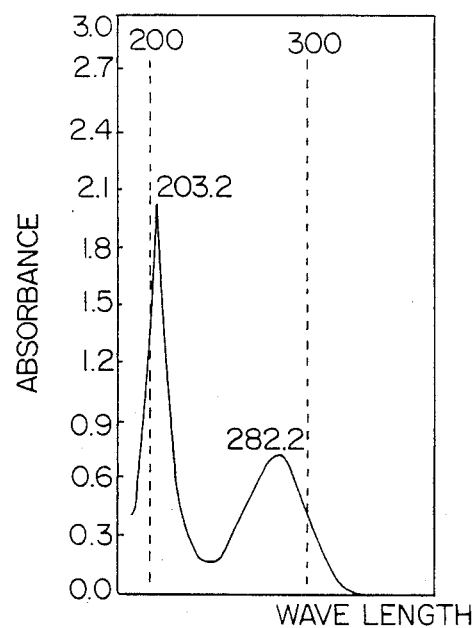
FIG. 1 represents the U.V. absorption spectrum of the product obtained in Example 1.
Figure 2:
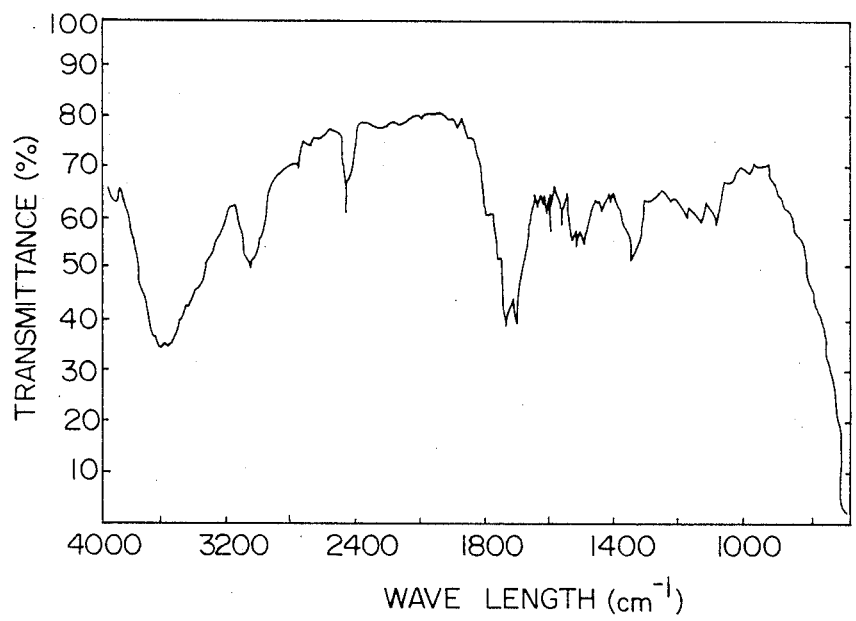
FIG. 2 represents the I.R. absorption spectrum of the product obtained in Example 1.
Figure 3:
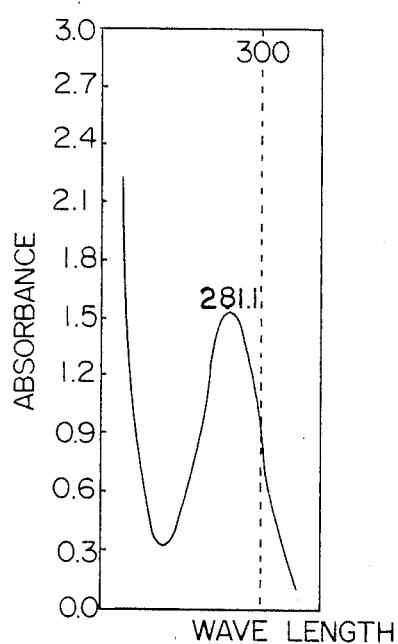
FIG. 3 represents the U.V. absorption spectrum of the product obtained in Example 2.
Figure 4:
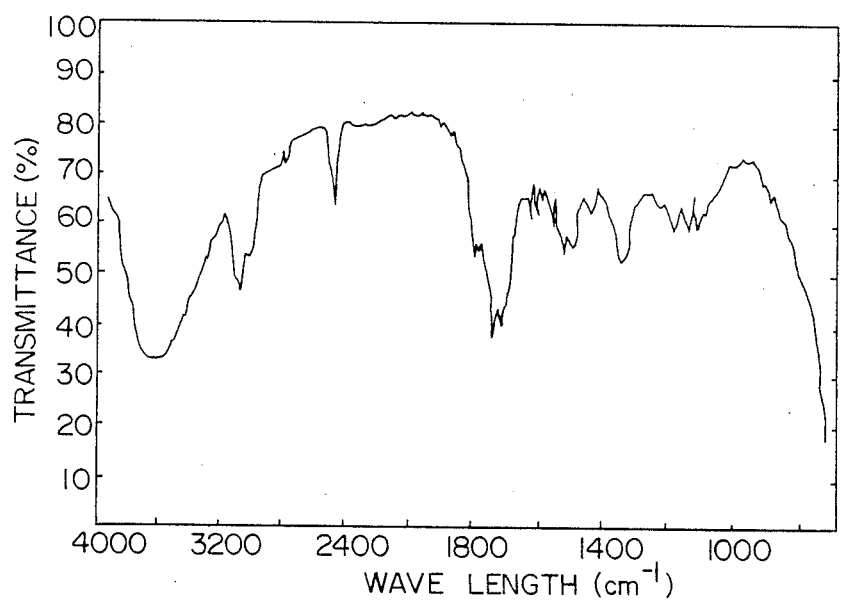
FIG. 4 represents the I.R. absorption spectrum of the product obtained in Example 2.

The present invention will now be further illustrated by the following examples.

EXAMPLE 1

10 g of vinylpyrrolidone/vinyl acetate polymer (Trademark: PVP/VA E-635, GAF Corporation U.S.A.) were introduced into 200 ml of 0.2N NaOH. The mixture was stirred for 2 hours at 60° C., adjusted to neutral with 1N HCl and subjected to ultrafiltration using a thin layer filter (Trademark: UM 10, AMICON, Holland) at 3 atoms. Evaporation under reduced pressure and lyophilization to a temperature of −70° C. to −80° C. gave 8.9 g of vinylpyrrolidone/vinyl alcohol polymer as white powder.

About 5,8 g of the above vinyl pyrrolidone/vinyl alcohol polymer were added to 40 ml of dichloromethane and swelled sufficiently with stirring slowly. To this mixture, 2.07 g (0.015 mol) of urocanic acid dissolved completely in 30 ml of dimethylformamide were added and then 1.62 g (0.01 mol) of 1,1-carbonyldiimidazole were added.

After carring out in a bath maintained to a constant temperature of 35° C. to 40° C. for 24 hours, the reaction was finished. The reaction mixture was filtered under reduced pressure and the insolubles were filtered off by the addition of 50 m of distilled water thereinto. The solution was adjusted to pH about 6.0 with 1N ACl and then lyophilized to give 6.9 g of compound (I) wherein R—O is the vinyl pyrrolidone/vinyl alcohol polymer.

EXAMPLE 2

5.8 g of vinyl pyrrolidone/vinylalcohol polymer prepared in Example 1 were added to 30 ml of dichloromethane to swell sufficiently. To this, 2.07 g (0.015 mol) of urocanic acid dissolved completely in 40 ml of dimethylformamide were added with stirring slowly. 3.09 g (0.015 mol) of N,N'-dicyclohexylcarbodiimide were dissolved in small amounts of dichloromethane and added to the resulting mixture. When the reaction was completed after stirring for 40 hours at 5° C. to 10° C., the solvent was removed using a rotary evaporator under reduced pressure. After adding 30 to 40 ml of distilled water thereinto, the insolubles were filtered off. Again, 100 to 110 ml of distilled water were poured and the low-molecular was removed by ultra-filtration. The aqueous layer containing the product was adjusted to PH 6.0 by the addition of 1N HCl, evaporated under reduced pressure, and lyophilized to give 6.1 g of reaction product;

D.S.: 0.08 millimol/g note: D.S.=degree of substitution.

EXAMPLE 3

10 g of vinyl formal/vinyl acetate polymer (Trademark: FCRMVAR, Monsanto Plastic & Resins Co.) were hydrolyzed in the same manner as in Example 1) to give 8.2 g of vinyl formal/vinyl alcohol/vinyl acetate polymer. After the above product was swelled sufficiently by the addition of 60 ml of dimethylformamide, 3.11 g (0.023 mol) of urocanic acid in 50 ml of dimethylformamide were added to the reactor and shaken for 10 minutes. To this, 4.61 g (0.023 mol) of N,N'-dicyclohexylcarbodiimide dissolved in small amounts of dichloromethane were added. After shaking the reactor for 28 hours at room temperature, the solvent was removed under reduced pressure. Again, 40 ml of distilled water were added and the insolubles were filtered off. The resulting solution was adjusted to pH 5.5 with 1N HCl and stood for 30 minutes. After ultrafiltration using a thin layer filter (trademark: UM10, AMICON, Holland) at 3 atoms, the low-molecular materials were filtered and the solution containing the product was concentrated and lyophilized to give about 6.5 g of reaction product;

D.S.: 0.1 millimol/g.

EXAMPLE 4

10 g of vinyl butyral/vinyl acetate polymer (Trademark: BUTVAR, Monsanto Plastics & Resins Co.) were subjected to hydrolysis in the same manner as in Example 1) to give 8.7 g of vinyl butyral/vinyl alcohol/vinyl acetate polymer. The product was charged into a synthetic container and reacted with a mixture of 4.28 g (0.025 mol) of N,N'-dicyclohexylcarbodiimide and 5.07 g (0.025 mol) of urocanic acid in 60 ml of dimethylformamide for 48 hours with shaking. After the reaction was completed, the solvent was removed under reduced pressure and the unreacted material was removed by using gel chromatography with Sephadex LH-20 column with methanol as an eluent.

The solvent was removed under reduced temperature to give 7.0 g of reaction product;

D.S.: 0.06 millimol/g.

EXAMPLE 5

6.8 g of alpha-[2-hydroxy-3-(trimethylammonio)-propyl]-ωhydroxypoly (oxy-1,2-ethandiyl)chloride cellulose-ω-ether (Trademark: UCARE Polymer JR-400. CTFA nomenclature: Polyquaternium-10, Union Carbide Corporation) were dispersed into 100 ml of dimethylformamide and stirred slowly for 30 minutes. 7.8 g of urocanic acid was added thereinto, stirred a few minutes, and introduced 11.14 g of dicyclohexylcarbodiimide immediately after dissolving in minimum amounts of dimethylformamide. After stirring overnight at room temperature, the reaction mixture was filtered and washed three times with isopropylalcohol and acetone. About 7.0 g of crude product were obtained after drying in a vaccum oven at 45° C. to a constant weight;

D.S.: 0.09 millimol/g.

We claim:

1. A novel cationic resin of the formula (I) wherein

R—O is a vinyl pyrrolidone/vinyl acetate/vinyl alcohol polymer, a vinyl pyrrolidone/vinyl alcohol polymer, a vinyl formal/vinyl alcohol/vinyl acetate polymer, or a vinyl butyral/vinyl alcohol/vinyl acetate polymer, and R' is a U.V. absorbing group of the formula

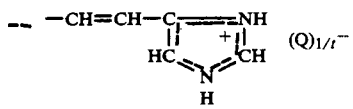

wherein t is an integer which is equal to the valence of Q and Q is chloride, bromide or iodide.

2. A resin of claim 1, wherein R—O is a vinyl pyrrolido/vinyl acetate/vinyl alcohol polymer.

3. A resin of claim 1, wherein R—O is a vinyl pyrrolidone/vinyl alcohol polymer.

4. A resin of claim 1, wherein R—O is a vinyl formal/vinyl alcohol/vinyl acetate polymer.

5. A resin of claim 1, wherein R—O is a vinyl butyral/vinyl alcohol/vinyl acetate polymer.

* * * * *